(12) United States Patent
Choi

(10) Patent No.: US 11,219,613 B2
(45) Date of Patent: Jan. 11, 2022

(54) PHARMACEUTICAL COMPOSITION FOR PREVENTING AND TREATING LIVER DISEASES, CONTAINING, AS ACTIVE INGREDIENT, CROMOLYN OR PHARMACEUTICALLY ACCEPTABLE SALT THEREOF

(71) Applicant: ONCOCROSS CO., LTD., Seoul (KR)

(72) Inventor: Jin Woo Choi, Seoul (KR)

(73) Assignee: ONCOCROSS CO., LTD., Seoul (KR)

( * ) Notice: Subject to any disclaimer, the term of this patent is extended or adjusted under 35 U.S.C. 154(b) by 165 days.

(21) Appl. No.: 16/776,267

(22) Filed: Jan. 29, 2020

(65) Prior Publication Data

US 2020/0345688 A1 Nov. 5, 2020

Related U.S. Application Data

(62) Division of application No. 15/754,845, filed as application No. PCT/KR2016/009368 on Aug. 24, 2016, now abandoned.

(30) Foreign Application Priority Data

Aug. 28, 2015 (KR) ........................ 10-2015-0122138

(51) Int. Cl.

| | |
|---|---|
| *A61K 31/366* | (2006.01) |
| *A61P 1/16* | (2006.01) |
| *A61K 31/35* | (2006.01) |
| *A61K 31/352* | (2006.01) |
| *A23L 33/10* | (2016.01) |
| *A23L 7/10* | (2016.01) |
| *A23L 13/60* | (2016.01) |
| *A23L 23/00* | (2016.01) |
| *A21D 2/14* | (2006.01) |
| *A23C 9/152* | (2006.01) |
| *A23L 2/52* | (2006.01) |

(52) U.S. Cl.
CPC ............. *A61K 31/366* (2013.01); *A21D 2/14* (2013.01); *A23C 9/1522* (2013.01); *A23L 2/52* (2013.01); *A23L 7/10* (2016.08); *A23L 13/60* (2016.08); *A23L 23/00* (2016.08); *A23L 33/10* (2016.08); *A61K 31/35* (2013.01); *A61K 31/352* (2013.01); *A61P 1/16* (2018.01); *A23V 2002/00* (2013.01)

(58) Field of Classification Search
CPC combination set(s) only.
See application file for complete search history.

(56) References Cited

U.S. PATENT DOCUMENTS

| 8,252,807 B2 | 8/2012 | Logsdon |
| 2009/0062319 A1 | 3/2009 | Logsdon et al. |
| 2015/0224077 A1 | 8/2015 | Gerhart et al. |

FOREIGN PATENT DOCUMENTS

| CA | 2938994 A1 | 8/2015 |
| KR | 20120107538 A | 10/2012 |
| KR | 20150038556 A | 4/2015 |
| RU | 2338745 C1 | 11/2008 |
| WO | 2014151326 A1 | 9/2014 |

OTHER PUBLICATIONS

"Chinese Application Serial No. 201680062320.7, Office Action dated May 13, 2019", w/ English Translation, (May 13, 2019), 13 pgs.
"European Application Serial No. 16842181.6, European Search Report dated Mar. 26, 2019", (Mar. 26, 2019), 9 pgs.
"Russian Application Serial No. 2018110607/04 Office Action dated Mar. 21, 2019", w/ English Translation, (Mar. 21, 2019), 7 pgs.
Hargrove, Laura, et al., "413 Inhibition of mast cell histamine secretion by cromolyn sodium treatment decreases BDL-induced liver inflammation and fibrosis", Hepatology vol. 60, No. 4-S1, (Aug. 1, 2014), 404A.
Kennedy, Lindsey L., et al., "Inhibition of mast cell-derived histamine secretion by cromolyn sodium treatment decreases biliary hyperplasia in cholestatic rodents", Laboratory Investigation 94.12, (Dec. 1, 2014), 1406-1418.
Pin-Jie, Huang, et al., "Effects of Anti-Histamine Treatment on Liver Injury", English Abstract Chinese Journal of Physiology vol. 57, No. 5 XP002788983, (Oct. 2014), 2 pgs.
Zhou, Xiqiao, et al., "Inhibition of Mast Cells Degranulation Protects Liver From LPS Induced Inflammation Through Hypothalamic-Pituitary-Thyroid Axis", Gastroenterology vol. 148, No. 4, (Apr. 1, 2015), S-1171.
"Canadian Application Serial No. 2996494, Office Action dated Dec. 14, 2018", (Dec. 14, 2018), 4 pgs.
"Chinese Application Serial No. 201680062320.7, Office Action dated Dec. 6, 2018", w/ English Translation, (Dec. 6, 2018), 14 pgs.
"International Application No. PCT/KR2016/009368, International Search Report dated Dec. 1, 2016", w/ English Translation, (Dec. 1, 2016), 7 pgs.
"International Application No. PCT/KR2016/009368, Written Opinion dated Dec. 1, 2016", (Dec. 1, 2016), 4 pgs.
Amiot, Laurence, et al., "Biology of the immunomodulatory molecule HLA-G in human liver diseases", Journal of hepatology 62.6, (2015), 1430-1437.
Amiot, Laurence, et al., "Expression of HLA-G by mast cells is associated with hepatitis C virus-induced liver fibrosis", Journal of hepatology 60.2, (2014), 245-252.
Bissell, D Montgomery, et al., "Cell-specific expression of transforming growth factor-beta in rat liver. Evidence for autocrine regulation of hepatocyte proliferation", The Journal of clinical investigation 96.1, (1995), 447-455.
Blakey, John D, et al., "Current progress in pharmacogenetics", British journal of clinical pharmacology 71.6, (2011), 824-831.

(Continued)

*Primary Examiner* — Heidi Reese
(74) *Attorney, Agent, or Firm* — Potomac Law Group, PLLC

(57) ABSTRACT

A pharmaceutical composition for preventing and treating liver diseases, includes cromolyn or a pharmaceutically acceptable salt thereof as an active ingredient.

6 Claims, 5 Drawing Sheets

(56) References Cited

OTHER PUBLICATIONS

Choi, Joon-Seok, et al., "Identification of cromolyn sodium as an anti-fibrotic agent targeting both hepatocytes and hepatic stellate cells", Pharmacological research 102, (Oct. 22, 2015), 176-183.

Choi, Joon-Seok, et al., "Identification of cromolyn sodium as an anti-fibrotic agent targeting both hepatocytes and hepatic stellate cells", Pharmacological research 102, (2015), 176-183.

Fend, Falko, et al., "Laser capture microdissection in pathology", Journal Clin Pathol 53, (2000), 66-672.

Friedman, Scott L, "Hepatic stellate cells: protean, multifunctional, and enigmatic cells of the liver", Physiological reviews 88.1, (2008), 125-172.

"Japanese Application Serial No. 2018-530451, Office Action dated Nov. 20, 2018", w/ English Translation, (Nov. 20, 2018), 6 pgs.

"Russian Application Serial No. 2018110607, Office Action dated Dec. 12, 2018", w/ English Translation, (Dec. 12, 2018), 13 pgs.

Jones, Hannah, et al., "Sa 1682 Mast Cell-Derived Histamine Includes the Progression of Fibrosis in the PSC Model of Mdr2-/- Mice", Gastroenterology V. 148 Iss. 4 Supp. 1, (Apr. 2015), S1010-S1011.

Kennedy, Lindsey L., et al., "Inhibition of mast cell-derived histamine secretion by cromolyn sodium treatment decreases biliary hyperplasia in cholestatic rodents", Laboratory Investigation 94.12, (2014), 1406-1418.

Motawi, Tarek, et al., "Evaluation of naproxen and cromolyn activities against cancer cells viability, proliferation, apoptosis, p53 and gene expression of survivin and caspase-3", Journal of enzyme inhibition and medicinal chemistry 29.2, (2014), 153-161.

Xiaohong, Liao, et al., "Experimental study of Disodium Cromoglycate against the Formation of Rat Liver Fibrosis", J. Huazhong Univ Sci Tech vol. 33 No. 6, (Dec. 2004), 726.

"Australian Application No. 2016316408 Office Action dated Nov. 6, 2018", 2 pgs.

"Australian Application Serial No. 2016316408 Office Action dated Aug. 23, 2018", (Aug. 23, 2018), 3 pgs.

"Korean Application No. 10-2015-0122138, Decision to Grant dated Oct. 24, 2016", w/ English Translation, (Oct. 24, 2016), 2 pgs.

"Korean Application No. 10-2015-0122138, Reason for Refusal dated Jun. 16, 2016", w/ English Translation, (Jun. 16, 2016), 6 pgs.

Friedman, Scott L., et al., "Isolated hepatic lipocytes and Kupffer cells from normal human liver: morphological and functional characteristics in primary culture", Hepatology 15.2, (1992), 234-243.

Giampieri, M. P., et al., "The lipocytes in normal human liver", Digestion 22.4, (1981), 165-169.

Gressner, Olav A, et al., "Connective tissue growth factor: a fibrogenic master switch in fibrotic liver diseases", Liver international 28.8, (2008), 1065-1079.

Henz, Beate M, "Exploring the mast cell enigma: a personal reflection of what remains to be done", Experimental dermatology 17.2, (2008), 91-99.

Hsu, Yi-Chao, et al., "Antifibrotic effects of Salvia miltiorrhiza on dimethylnitrosamine-intoxicated rats", Journal of biomedical science 12.1, (2005), 185-195.

Huang, Guangcun, et al., "Regulation of hepatic stellate cells by connective tissue growth factor", Front Biosci 17.2, (2012), 2495-2507.

Huettner, James E, et al., "Block of N-methyl-D-aspartate-activated current by the anticonvulsant MK-801: selective binding to open channels", Proceedings of the National Academy of Sciences 85.4, (1988), 1307-1311.

Iredale, John P, "Models of liver fibrosis: exploring the dynamic nature of inflammation and repair in a solid organ", The Journal of clinical investigation 117.3, (2007), 539-548.

Ishii, M, et al., "A role of mast cells for hepatic fibrosis in primary sclerosing cholangitis", Hepatology research 31.3, (2005), 127-131.

Iwaisako, Keiko, et al., "What's new in liver fibrosis? The origin of myofibroblasts in liver fibrosis", Journal of qastroenterology and hepatoloqy 27.s2, (2012), 65-68.

Jeong, Da-Hee, et al., "Alterations of mast cells and TGF-B1 on the silymarin treatment for CCl4-induced hepatic fibrosis", World journal of gastroenterology: WJG 11.8, (2005), 1141-1148.

Jin, Y. L., et al., "Effects of mast cells on degradation of collagen fibers in dimethylnitrosamine-induced hepatic fibrosis of rat", Zhonghua bing li xue za zhi= Chinese journal of pathology 41.4, (2012), 260-264.

Kanellakis, Peter, et al., "A pro-fibrotic role for interleukin-4 in cardiac pressure overload", Cardiovascular research 95.1, (2012), 77-85.

Kim, Taehyun, et al., "Cell type-specific gene expression profiling in brain tissue: comparison between TRAP, LCM and RNA-seq", BMB reports 48.7, (2015), 388-394.

Lamb, Justin, et al., "The Connectivity Map: using gene-expression signatures to connect small molecules, genes, and disease", science 313.5795, (2006), 1929-1935.

Mauviel, Alain, "Transforming growth factor-ls signaling in skin: stromal to epithelial cross-talk", Journal of Investigative Dermatology 129.1, (2009), 7-9.

Mogler, Carolin, et al., "Hepatic stellate cell-expressed endosialin balances fibrogenesis and hepatocyte proliferation during liver damage", EMBO molecular medicine 7.3, (2015), 332.

Neef, Markus, et al., "Oral imatinib treatment reduces early fibrogenesis but does not prevent progression in the lonq term", Journal of hepatoloqy 44.1, (2006), 167-175.

Patsenker, Eleonora, et al., "Role of integrins in fibrosing liver diseases", American journal of physiology-qastrointestinal and liver physiology 301.3, (2011), G425-G434.

Renko, Kostja, et al., "Identification of iopanoic acid as substrate of type 1 deiodinase by a novel nonradioactive odide-release assay", Endocrinology 153.5, (2012), 2506-2513.

References Are Not Being Filed Herewith. They Are Already of Record in One or More of the Following Applications, Which Are Being Relied on for Priority Under 35 U.S.C. Section 120 (see 37 C.F.R. Section 1.98(d)(1)): U.S. Appl. No. 15/754,845 having 371(c) date of Feb. 23, 2018.

Schmitt, James K, et al., "Altering therapy of type II diabetes mellitus from insulin to tolazamide increases blood pressure in spite of weight loss", American journal of hypertension 8.5, (1995), 520-523.

Schuppan, Detlef, et al., "Evolving therapies for liver fibrosis", The Journal of clinical investiqtation 123.5, (2013), 1887-1901.

Tzeng, Jann-Inn, et al., "Silymarin decreases connective tissue growth factor to improve liver fibrosis in rats treated with carbon tetrachloride", Phytotherapy Research 27.7, (2013), 1023-1028.

Veerappan, Arul, et al., "Mast cells: a pivotal role in pulmonary fibrosis", DNA and cell biology 32.4, (2013), 206-218.

Wei, Guo, et al., "Gene expression-based chemical genomics identifies rapamycin as a modulator of MCL1 and qlucocorticoid resistance", Cancer cell 10.4, (2006), 331-342.

Wen, Shi-Lei, et al., "Celecoxib attenuates hepatic cirrhosis through inhibition of epithelial-to-mesenchymal transition of hepatocytes", Journal of gastroenterology and hepatology 29.11, (2014), 1932-1942.

Wiemann, Stefanie U, et al., "Hepatocyte telomere shortening and senescence are general markers of human liver cirrhosis". The FASEB journal 16.9, (2002), 935-942.

Yang, M., et al., "Preconditioning Donor Livers With Cromolyn or Compound 48/80 Prolongs Recipient Survival in a Rat Orthotopic Liver Transplantation Model", Transplantation proceedings. vol. 46. No. 5. Elsevier, (2014), 1554-1559.

Yao, Qun-Yan, et al., "Inhibition by curcumin of multiple sites of the transforming growth factor-beta1 signalling pathway ameliorates the progression of liver fibrosis induced by carbon tetrachloride in rats", BMC complementary and alternative medicine 12.1, (2012), 156.

Zhang, Chunqing, et al., "Effects of Ginkgo biloba extract on cell proliferation, cytokines and extracellular matrix of hepatic stellate cells", Liver International 26.10, (2006), 1283-1290.

References Are Not Being Filed Herewith. They Are Already of Record in One or More of the Following Applications, Which Are

(56) References Cited

OTHER PUBLICATIONS

Being Relied on for Priority Under 35 U.S.C. Section 120 (see 37 C.F.R. Section 1.98(d)(1)): U.S. Appl. No. 15/754,845 having a 371(c) date of Feb. 23, 2018.
Chinese Third Office Action dated Sep. 5, 2019 in corresponding Chinese Application No. 201680062320.7 (with English language machine translation).
European Office Action (Communication pursuant to Article 94(3) EPC) dated Nov. 6, 2020, issued in European Application No. 16842181.6.
Indian Examination Report dated Jun. 27, 2019 in corresponding Indian Application No. 201817008424 (with English translation).
Japanese Office Action (Notice of Reasons for Refusal) dated Nov. 4, 2020, issued in Japanese Application No. 2018-530451 (with English language machine translation).
Otani, "Cellular senescence and chronic inflammation," Japanese Journal of Clinical Immunology, Oct. 2014, vol. 37(5), pp. 390-397, The Japan Society of Clinical Immunology, Tokyo, Japan (with English language machine translation).
Saito, "Trans-differentiation of cancer cells and TGF-β," Yamanashi Magazine, 2012, vol. 26(1), pp. 9-14 (with English language machine translation).
Yanguas et al., "Experimental models of liver fibrosis," Archives of Toxicology, May 2016, vol. 90, pp. 1025-1048, Springer, Berlin, Germany.

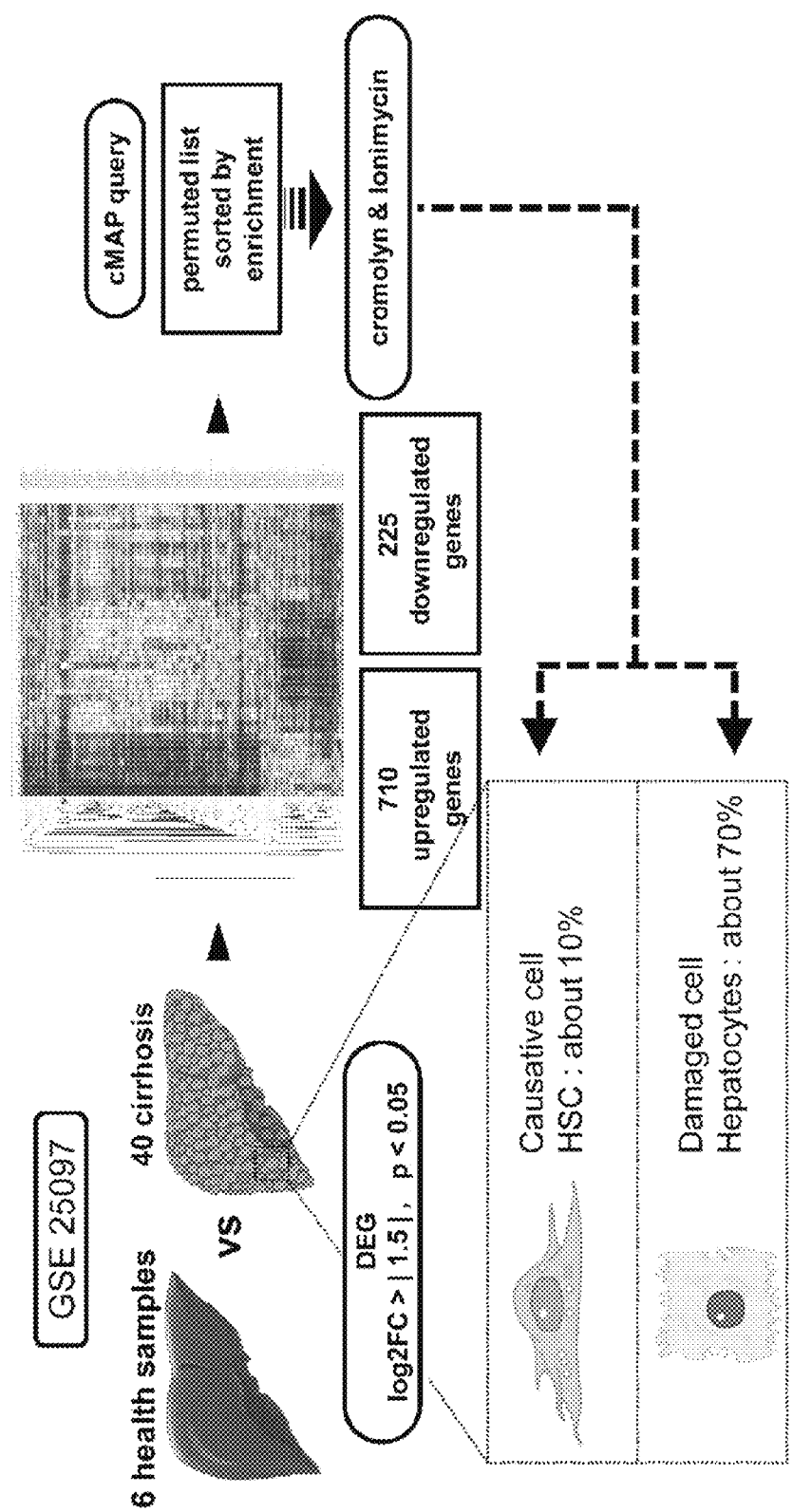

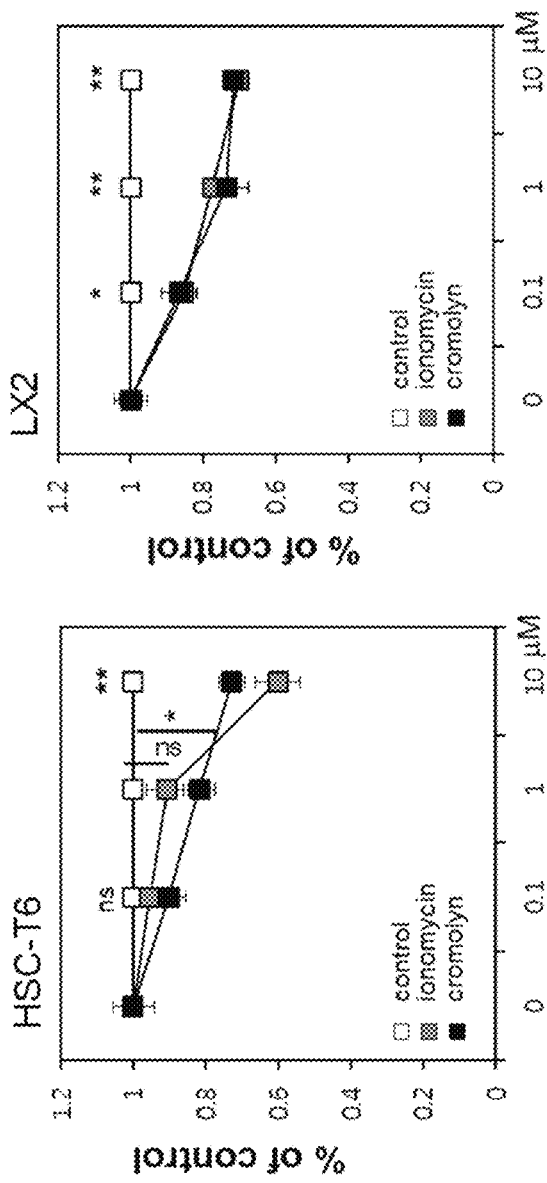
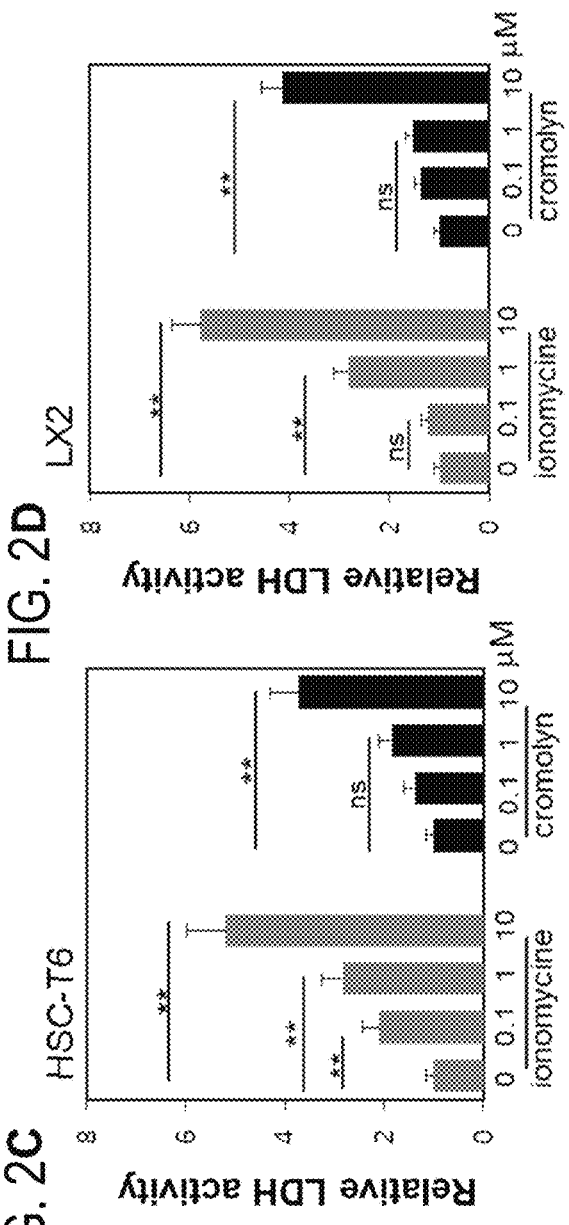
FIG. 2A  FIG. 2B  FIG. 2C  FIG. 2D

PHARMACEUTICAL COMPOSITION FOR PREVENTING AND TREATING LIVER DISEASES, CONTAINING, AS ACTIVE INGREDIENT, CROMOLYN OR PHARMACEUTICALLY ACCEPTABLE SALT THEREOF

TECHNICAL FIELD

The present invention relates to a pharmaceutical composition for preventing or treating various liver diseases including liver cirrhosis, containing cromolyn or a pharmaceutically acceptable salt thereof as an active ingredient.

BACKGROUND

Liver fibrosis (hepatic fibrosis) is the excessive accumulation of fibers in the liver that results from liver disorders, which could have been caused by acute damage such as damage to the liver cells due to hepatitis C or hepatitis B virus, alcohol, toxins, etc. Reversible wound-healing reactions against the damage reflect an important balance between liver repair and scar formation (see Reference Document No. 1). Chronic damage gradually replaces liver parenchyma to scar tissues, thereby eventually resulting in liver cirrhosis. Fibrosis is also relevant to excessive wound-healing reaction which is caused by the excessive accumulation of scar tissues such as extracellular matrix. When fibrosis spreads in the liver, liver cirrhosis is caused, and consequently, complications such as hepatic failure and hepatocellular carcinoma are caused which can lead to patient deaths.

Hepatic stellate cell (HSC) is a type of cell which triggers diseases, and is an important contributor to liver cirrhosis development caused by various causes of diseases such as infection with the hepatitis virus and alcohol consumption (see Reference Document No. 2). When HSC is activated, extracellular matrix components, for example, collagen, are accumulated excessively, and this results in the distortion of the hepatic vasculature and architecture and increase in portal pressure, thereby causing the relevant symptoms. Such series of events, in turn, activate HSC again, thus forming a detrimental cycle which triggers the process of liver cirrhosis (hepatocirrhosis) (see Reference Document No. 3). HSC proliferation and activation are mediated by various signaling (see Reference Document No. 4), and since HSC signaling inhibitors have the potential to be developed as antifibrotic agents they have been studied continuously. The antifibrotic effects of several synthetic compounds and biological drugs relate to HSC proliferation-related growth factors and related signaling pathways which reduce the proliferative response of HSC (see Reference Document Nos. 5 and 6).

For instance, curcumin (see Reference Document No. 7), a plant extract containing silymarin (see Reference Document No. 8), Ginkgo biloba extract (see Reference Document No. 9), and Salvia extract (see Reference Document No. 10) have been reported to activate myofibroblasts, inhibit connective tissue growth factors accumulated in the liver (see Reference Document No. 11), and stimulate the release of the components of fiber formation, thus inhibiting the TGF-β pathway which contributes to the profibrogenic pathway (see Reference Document No. 12).

As the fibrosis process progresses by HSC, hepatocyte damage becomes more severe. During fibrosis, hepatocytes go through epithelial mesenchymal transition (EMT) (see Reference Document Nos. 13 and 14) and senescence due to telomere shortening (see Reference Document No. 15). As a result, hepatocytes lose their function, and hepatic failure occurs. Although most studies on treatment agents for hepatic fibrosis or liver cirrhosis focus on HSC, HSC constitutes less than 15% of liver, while hepatocytes occupy up to 70% of the liver tissue, which are the parenchymal cells of the liver (see Reference Document Nos. 16 and 17). Therefore, in developing a new drug for the treatment of liver cirrhosis, the protection or recovery of the hepatocytes from chronic damage is very important. Such pharmacological strategy was developed as an effective tool for discovering the chemical substance candidates, which are regulators, based on the gene expression (see Reference Document No. 18). The above approach can be used for re-designing a new drug for treating a disease and developing a new drug.

In addition, a connectivity map is a noteworthy algorithm that is used for evaluating the chemical substance candidates which alter gene expression (see Reference Document Nos. 19 and 20). The above pharmacological strategy is to identify a candidate substance which is expected to show high functionality in vivo and may make the drug development process more effective.

Meanwhile, cromolyn is a compound which prevents the secretion of histamine and leukotriene from sensitized mast cells in the mucous membrane of the lung and eyes, and is known to indirectly prevent the calcium ions from entering the cells, even though its exact working mechanism is not known yet. Furthermore, cromolyn is known to inhibit secondary bronchospasm caused by tachykinin by inhibiting neural reflex in the lung, and is known to inhibit the migration of immunocytes such as neutrophils, monocytes, eosinophils, etc. and to downregulate the beta-2 functional groups of lymphocytes. However, its effect with respect to various liver diseases including liver cirrhosis is not known.

Accordingly, as a result of the present inventors' effort to develop a fundamental therapeutic agent for liver cirrhosis, it was found that cromolyn, which was selected by the connectivity map, inhibits the accumulation of collagen and the production of TGF-β, which are known as the major secretion marker of hepatic stellate cells (HSCs) and also suppresses hepatocyte migration caused by TGF-β. Further, cromolyn was found to inhibit the decrease of E-cadherin expression resulting from EMT progression and have an anti-senescence effect on hepatocytes. As a result, the present invention was completed by finding that cromolyn has the dual effect of inhibiting the activity of HSCs and promoting the recovery of hepatocyte function, and thus is capable of being used as a fundamental therapeutic agent for liver cirrhosis.

PRIOR ART DOCUMENTS

Non-Patent Documents (Non-Patent Document 1) [1] Mogler C, Wieland M, Konig C, et al. Hepatic stellate cell-expressed endosialin balances fibrogenesis and hepatocyte proliferation during liver damage. EMBO molecular medicine. 2015; 7: 332-8.

(Non-Patent Document 2) [2] Huang G, Brigstock D R. Regulation of hepatic stellate cells by connective tissue growth factor. Frontiers in bioscience. 2012; 17: 2495-507.

(Non-Patent Document 3) [3] Iredale J P. Models of liver fibrosis: exploring the dynamic nature of inflammation and repair in a solid organ. The Journal of clinical investigation. 2007; 117: 539-48.

(Non-Patent Document 4) [4] Friedman S L. Hepatic stellate cells: protean, multifunctional, and enigmatic cells of the liver. Physiological reviews. 2008; 88: 125-72.

(Non-Patent Document 5) [5] Neef M, Ledermann M, Saegesser H, et al. Oral imatinib treatment reduces early fibrogenesis but does not prevent progression in the long term. Journal of hepatology. 2006; 44: 167-75.

(Non-Patent Document 6) [6] Patsenker E, Stickel F. Role of integrins in fibrosing liver diseases. American journal of physiology Gastrointestinal and liver physiology. 2011; 301: G425-34.

(Non-Patent Document 7) [7] Yao Q Y, Xu B L, Wang J Y, Liu H C, Zhang S C, Tu C T. Inhibition by curcumin of multiple sites of the transforming growth factor-beta1 signalling pathway ameliorates the progression of liver fibrosis induced by carbon tetrachloride in rats. BMC complementary and alternative medicine. 2012; 12: 156.

(Non-Patent Document 8) [8] Tzeng J I, Chen M F, Chung H H, Cheng J T. Silymarin decreases connective tissue growth factor to improve liver fibrosis in rats treated with carbon tetrachloride. Phytotherapy research: PTR. 2013; 27: 1023-8.

(Non-Patent Document 9) [9] Zhang C, Zhu Y, Wan J, Xu H, Shi H, Lu X. Effects of *Ginkgo biloba* extract on cell proliferation, cytokines and extracellular matrix of hepatic stellate cells. Liver international: official journal of the International Association for the Study of the Liver. 2006; 26: 1283-90.

(Non-Patent Document 10) [10] Hsu Y C, Lin Y L, Chiu Y T, Shiao M S, Lee C Y, Huang Y T. Antifibrotic effects of *Salvia* miltiorrhiza on dimethylnitrosamine-intoxicated rats. Journal of biomedical science. 2005; 12: 185-95.

(Non-Patent Document 11) [11] Gressner O A, Gressner A M. Connective tissue growth factor: a fibrogenic master switch in fibrotic liver diseases. Liver international: official journal of the International Association for the Study of the Liver. 2008; 28: 1065-79.

(Non-Patent Document 12) [12] Mauviel A. Transforming growth factor-beta signaling in skin: stromal to epithelial cross-talk. The Journal of investigative dermatology. 2009; 129: 7-9.

(Non-Patent Document 13) [13] Wen S L, Gao J H, Yang W J, et al. Celecoxib attenuates hepatic cirrhosis through inhibition of epithelial-to-mesenchymal transition of hepatocytes. Journal of gastroenterology and hepatology. 2014; 29: 1932-42.

(Non-Patent Document 14) [14] Iwaisako K, Brenner D A, Kisseleva T. What's new in liver fibrosis? The origin of myofibroblasts in liver fibrosis. Journal of gastroenterology and hepatology. 2012; 27 Supp12: 65-8.

(Non-Patent Document 15) [15] Wiemann S U, Satyanarayana A, Tsahuridu M, et al. Hepatocyte telomere shortening and senescence are general markers of human liver cirrhosis. FASEB journal: official publication of the Federation of American Societies for Experimental Biology. 2002; 16: 935-42.

(Non-Patent Document 16) [16] Giampieri M P, Jezequel A M, Orlandi F. The lipocytes in normal human liver. A quantitative study. Digestion. 1981; 22: 165-9.

(Non-Patent Document 17) [17] Friedman S L, Rockey D C, McGuire R F, Maher J J, Boyles J K, Yamasaki G. Isolated hepatic lipocytes and Kupffer cells from normal human liver: morphological and functional characteristics in primary culture. Hepatology. 1992; 15: 234-43.

(Non-Patent Document 18) [18] Blakey J D, Hall I P. Current progress in pharmacogenetics. British journal of clinical pharmacology. 2011; 71: 824-31.

(Non-Patent Document 19) [19] Lamb J, Crawford E D, Peck D, et al. The Connectivity Map: using gene-expression signatures to connect small molecules, genes, and disease. Science. 2006; 313: 1929-35.

(Non-Patent Document 20) [20] Wei G, Twomey D, Lamb J, et al. Gene expression-based chemical genomics identifies rapamycin as a modulator of MCL1 and glucocorticoid resistance. Cancer cell. 2006; 10: 331-42.

(Non-Patent Document 21) [21] Huettner J E, Bean B P. Block of N-methyl-D-aspartate-activated current by the anticonvulsant MK-801: selective binding to open channels. Proceedings of the National Academy of Sciences of the United States of America. 1988; 85: 1307-11.

(Non-Patent Document 22) [22] Schmitt J K, Johns S B. Altering therapy of type II diabetes mellitus from insulin to tolazamide increases blood pressure in spite of weight loss. American journal of hypertension. 1995; 8: 520-3.

(Non-Patent Document 23) [23] Renko K, Hoefig C S, Hiller F, Schomburg L, Kohrle J. Identification of iopanoic acid as substrate of type 1 deiodinase by a novel nonradioactive iodide-release assay. Endocrinology. 2012; 153: 2506-13.

(Non-Patent Document 24) [24] Bissell D M, Wang S S, Jarnagin W R, Roll F J. Cell-specific expression of transforming growth factor-beta in rat liver. Evidence for autocrine regulation of hepatocyte proliferation. The Journal of clinical investigation. 1995; 96: 447-55.

(Non-Patent Document 25) [25] Schuppan D, Kim Y O. Evolving therapies for liver fibrosis. The Journal of clinical investigation. 2013; 123: 1887-901.

(Non-Patent Document 26) [26] Kanellakis P, Ditiatkovski M, Kostolias G, Bobik A. A pro-fibrotic role for interleukin-4 in cardiac pressure overload. Cardiovascular research. 2012; 95: 77-85.

(Non-Patent Document 27) [27] Veerappan A, O'Connor N J, Brazin J, et al. Mast cells: a pivotal role in pulmonary fibrosis. DNA and cell biology. 2013; 32: 206-18.

(Non-Patent Document 28) [28] Henz B M. Exploring the mast cell enigma: a personal reflection of what remains to be done. Experimental dermatology. 2008; 17: 91-9.

(Non-Patent Document 29) [29] Amiot L, Vu N, Rauch M, et al. Expression of HLA-G by mast cells is associated with hepatitis C virus-induced liver fibrosis. Journal of hepatology. 2014; 60: 245-52.

(Non-Patent Document 30) [30] Ishii M, Iwai M, Harada Y, et al. A role of mast cells for hepatic fibrosis in primary sclerosing cholangitis. Hepatology research: the official journal of the Japan Society of Hepatology. 2005; 31: 127-31.

(Non-Patent Document 31) [31] Jeong D H, Lee G P, Jeong W I, et al. Alterations of mast cells and TGF-beta1 on the silymarin treatment for CCl(4)-induced hepatic fibrosis. World journal of gastroenterology: WJG. 2005; 11: 1141-8.

(Non-Patent Document 32) [32] Jin Y L, Zhou Q, Tian C, Liu H G, Hayashi Y, Enzan H [Effects of mast cells on degradation of collagen fibers in dimethylnitrosamine-induced hepatic fibrosis of rat]. Zhonghua bing li xue za zhi Chinese journal of pathology. 2012; 41: 260-4.

(Non-Patent Document 33) [33] Amiot L, Vu N, Samson M. Biology of the immunomodulatory molecule HLA-G in human liver diseases. Journal of hepatology. 2015.

(Non-Patent Document 34) [34] Fend F, Raffeld M. Laser capture microdissection in pathology. Journal of clinical pathology. 2000; 53: 666-72.

(Non-Patent Document 35) [35] Kim T, Lim C S, Kaang B K. Cell type-specific gene expression profiling in brain tissue: Comparison among TRAP, LCM and RNA-seq. BMB reports. 2015.

DETAILED DESCRIPTION OF THE INVENTION

Technical Problem to be Solved

The object of the present invention relates to a pharmaceutical composition and health food for preventing and treating liver diseases comprising cromolyn or a pharmaceutically acceptable salt thereof as an active ingredient.

Means for Solving the Problem

In order to achieve the above object, the present invention provides a pharmaceutical composition for preventing and treating liver diseases comprising cromolyn or a pharmaceutically acceptable salt thereof as an active ingredient.

In addition, the present invention provides health food for preventing and ameliorating liver diseases comprising cromolyn or a pharmaceutically acceptable salt thereof as an active ingredient.

Effect of the Invention

The cromolyn of the present invention or its pharmaceutically acceptable salt inhibits the accumulation of collagen and the production of TGF-β, which are known as the major secretion marker of hepatic stellate cells (HSCs), and also suppresses hepatocyte migration caused by TGF-β. Further, it inhibits the decrease of E-cadherin expression resulting from EMT progression and has an anti-senescence effect on hepatocytes. As a result, cromolyn has the dual effect of inhibiting the activity of HSCs and promoting the recovery of hepatocyte function, and thus can be used as a fundamental therapeutic agent for various liver diseases including liver cirrhosis.

BRIEF DESCRIPTION OF THE DRAWINGS

FIG. 1 depicts a method for identifying an anti-liver cirrhosis candidate agent using the connectivity map.

FIGS. 2A, 2B, 2C, and 2D verify the effects on the proliferation and cytotoxicity of hepatic stellate cell (HSC) by using the candidate agent of the present invention:

FIG. 2A: HSC-T6 cell line was treated with the untreated control, cromolyn, and ionomycin, respectively, and then the effects on cell proliferation were confirmed by MTT assay;

FIG. 2B: LX-2 cell line was treated with the untreated control, cromolyn, and ionomycin, respectively, and then the effects on cell proliferation were confirmed by MTT assay;

FIG. 2C: HSC-T6 cell line was treated with cromolyn and ionomycin, respectively, in different concentrations, and then the effects on cytotoxicity were confirmed by LDH assay; and FIG. 2D: LX-2 cell line was treated with cromolyn and ionomycin, respectively, in different concentrations, and then the effects on cytotoxicity were confirmed by LDH assay.

FIG. 3A: shows the relative amount of collagen in the HSC-T6 and LX-2 cell lines after treating with cromolyn in different concentrations; and FIG. 3B: shows the relative amount of TGF-β in the HSC-T6 and LX-2 cell lines after treating with cromolyn in different concentrations.

FIG. 4A: verifies the effects of cromolyn on cell motility at 0 and 48 hours after treating with cromolyn, with or without TGF-β (2 ng/mL) through the wound analysis using a microscope (Scale bar: 100 μm);

FIG. 4B: measured the wound healing distance, and then shows it in relative percentage by comparing with the distance at 0 hour of the treatment with cromolyn; and FIG. 4C: verifies the changes in the expression of E-cadherin.

FIG. 5A: verifies the anti-senescence effect through β-galactosidase staining after treating with cromolyn; and FIG. 5B: verifies the β-galactosidase-positive cells at 3 days after the isolation of primary hepatocytes through a microscope.

EMBODIMENTS

The present invention will be described below in more detail.

The present invention provides a pharmaceutical composition for preventing and treating liver diseases comprising cromolyn or a pharmaceutically acceptable salt thereof as an active ingredient.

The cromolyn is a compound represented as [Formula 1] below.

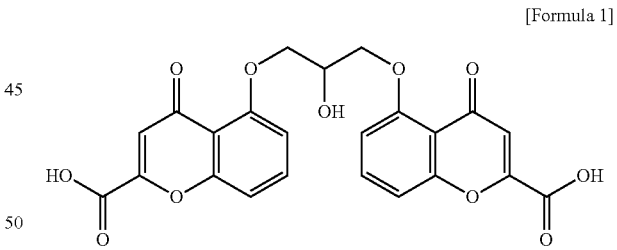

[Formula 1]

Preferably, the cromolyn inhibits the activity of hepatic stellate cell (HSC) and promotes the recovery of hepatocyte function; more preferably, the inhibition of HSC activity inhibits the accumulation of collagen and the production of TGF-β in HSCs; and more preferably the recovery of hepatocyte function is that the cromolyn shows a significant inhibition of the decrease in E-cadherin expression caused by EMT progression in hepatocytes and anti-senescence effect on hepatocytes, but are not limited to the above.

The liver diseases are preferably selected from the group consisting of liver cirrhosis, liver fibrosis, liver failure, liver cancer, and hepatitis, and more preferably are liver cirrhosis, liver fibrosis, and liver failure.

In the specific embodiment of the present invention, the present inventors primarily selected the anti-liver cirrhosis candidate agents by using the connectivity map (see Table 1 and FIG. 1), and then selected cromolyn and ionomycin in consideration of the side effects for the second time.

Further, the present inventors selected cromolyn as the final candidate agent through confirmation of the effect on cytotoxicity with respect to HSCs since ionomycin has the possibility of cytotoxicity (see FIG. 2).

In addition, the present inventors confirmed whether cromolyn inhibits the accumulation of collagen and the production of TGF-β, which are known as the major secretion marker of activated HSCs. As a result, they found that cromolyn reduces the accumulation of collagen and inhibits the production of TGF-β in a concentration-dependent manner (see FIG. 3).

Furthermore, the present inventors confirmed the inhibitory effect of cromolyn on hepatocyte EMT (epithelial-mesenchymal transition). As a result, they found that cromolyn effectively inhibits the migration activity of hepatocytes and significantly inhibits the decrease in E-cadherin expression (see FIG. 4).

Figure 5A:
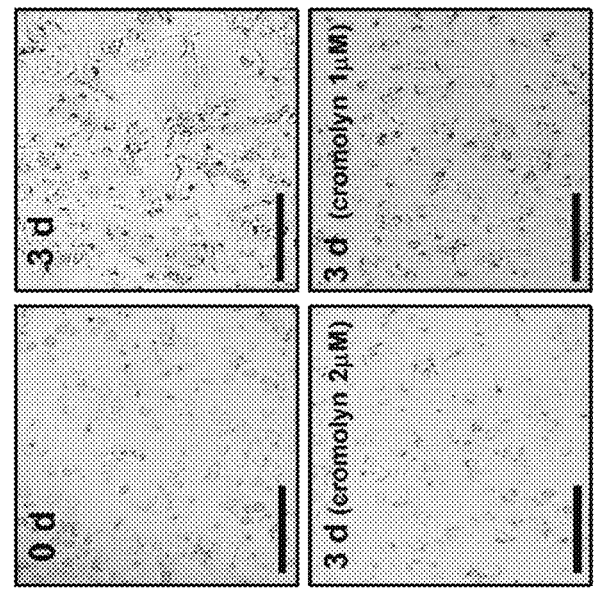
FIGS. 5A and 5B verify the effect of cromolyn on the production of β-galactosidase.
Figure 5B:
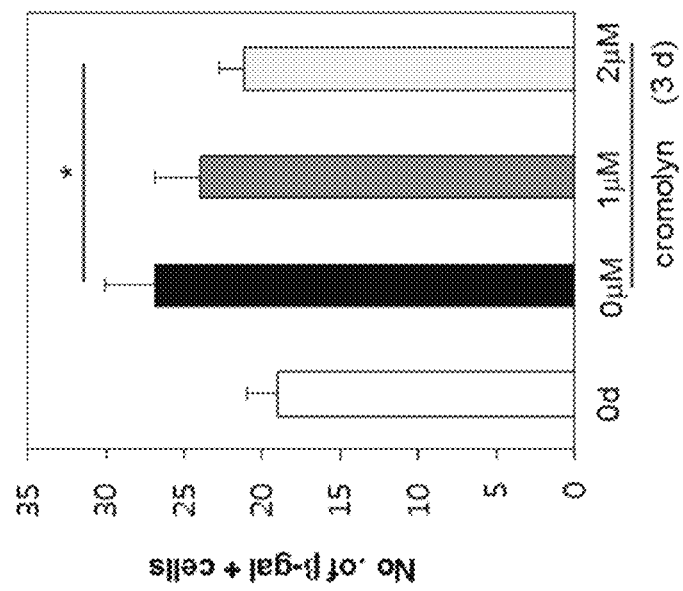

Further, the present inventors confirmed the anti-senescence effect of cromolyn on hepatocytes, and found that cromolyn has a significant anti-senescence effect on hepatocytes (see FIG. 5).

Therefore, the cromolyn of the present invention not only inhibits the production of TGF-β and the accumulation of collagen, which are known as the major secretion marker of HSCs, but also inhibits hepatocyte migration caused by the treatment of hepatocytes with TGF-β, inhibits the decrease in E-cadherin expression caused by EMT progression, and shows an anti-senescence effect on hepatocytes, thereby showing the dual effect of inhibiting the activity of HSCs as well as promoting the recovery of hepatocyte function. Therefore, the cromolyn of the present invention can be used as a fundamental pharmaceutical composition for treating various liver diseases including liver cirrhosis.

The present invention includes not only the cromolyn represented by Formula 1, but also all of its pharmaceutically acceptable salts and solvates, hydrates, racemates, or stereoisomers which can be manufactured therefrom.

The cromolyn of the present invention that is represented by Formula 1 can be used in the form of a pharmaceutically acceptable salt, and as the salt, the acid addition salts formed by a pharmaceutically acceptable free acid are useful. The acid addition salts are obtained from mineral acids such as hydrochloric acid, nitric acid, phosphoric acid, sulfuric acid, hydrobromic acid, hydroiodic acid, nitrous acid or phosphorous acid, and nontoxic organic acids such as aliphatic mono and dicarboxylate, phenyl-substituted alkanoate, hydroxyl alkanoate and alkandioate, aromatic acids, aliphatic and aromatic sulfonic acid. Such pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluene sulfonate, chlorobenzenesulfonate, xylene sulfonate, phenyl acetate, phenyl propionate, phenyl butyrate, citrate, lactate, hydroxy butyrate, glycollate, malate, tartrate, methane sulfonate, propane sulfonate, naphthalene-1-sulfonate, naphthalene-2-sulfonate, or mandelate.

The acid addition salt according to the present invention can be prepared by common methods, for example, by dissolving the cromolyn represented by Formula 1 in an excess amount of acid solution, and precipitating the above salt by using a water-compatible organic solvent, for instance, methanol, ethanol, acetone or acetonitrile. Further, it can be prepared by drying through evaporating the solvent or the excess amount of acid in the mixture or conducting suction filtration of the precipitated salt.

In addition, a pharmaceutically acceptable metallic salt can be prepared by using a base. For example, salts of alkali metal or alkaline earth metal are obtained by dissolving a compound in an excess amount of the solution of alkali metal hydrides or alkaline earth metal hydrides, filtering the salt of the non-soluble compound, and evaporating and drying the residual solution. Here, it is pharmaceutically appropriate to prepare a sodium, potassium, or calcium salt as the metallic salt. Further, a silver salt corresponding to the above is obtained by reacting an alkali metal or alkaline earth metal salt with an appropriate negative salt (e.g., silver nitrate).

When formulating the above composition as a formulation, the formulation is prepared by using a commonly-used filler, extender, binding agent, wetting agent, disintegrating agent, diluent such as surfactant, etc. or excipient.

A solid preparation for oral administration includes a tablet, pill, powder, granule, capsule, troche, etc., and such a solid preparation is prepared by mixing cromolyn represented by Formula 1 with at least one excipient, for example, starch, calcium carbonate, sucrose or lactose or gelatin, etc. Further, lubricants other than a simple excipient, such as magnesium stearate, talc are also used. A liquid preparation for oral administration includes a suspension, a liquid preparation for internal use, emulsion, or syrup, etc., and various excipients other than water and liquid paraffin, which are simple diluents, such as a wetting agent, sweetening agent, flavoring agent, preservative, etc. can be included.

In the parenteral preparation, a sterilized solution, non-aqueous solution, suspension solution, emulsion, lyophilized preparation, suppository preparation, etc. are included.

As a non-aqueous solution and suspension solution, propylene glycol, polyethylene glycol, vegetable oils such as olive oil, injectable esters such as ethyl oleate, etc. can be used. Witepsol, Macrogol, Tween 61, cacao butter, laurinum, glycerol, gelatin, etc. can be used as substrates for the suppository preparation.

The composition according to the present invention is administered in a pharmaceutically effective amount. In the present invention, "a pharmaceutically effective amount" indicates an amount sufficient to treat the disease with a reasonable benefit/risk ratio that can be applied to medical treatment, and the level of effective dose can be determined depending on factors including the type of disease, severity of symptoms, activity of the drug, sensitivity to the drug, administration time, administration route and excretion ratio, treatment period, concurrently used drugs, and other factors that are well known in the medical field. The composition of the present invention can be administered individually as a single drug or co-administered with other drugs; can be administered subsequently or concurrently with the conventional drugs; and can be administered in a single dose or multiple doses. It is important to administer the minimum amount that can achieve the maximum effect without the side effects considering all of the above factors, and this can be easily determined by a person skilled in the art.

Specifically, the effective dose of the compound according to the present invention may vary depending on the age, gender, weight of the patient, and generally, it can be administered 0.1 mg-100 mg per 1 kg of weight, preferably 0.5 mg-10 mg daily or every other day, or administered once, twice, or three times per day. However, the effective dose can be increased or decreased depending on the administration route, severity of obesity, gender, weight, age, etc., and thus, the above dose does not limit the scope of the present invention in any way.

In addition, the present invention provides health food for preventing or ameliorating liver diseases, which comprises cromolyn or a pharmaceutically acceptable salt thereof as an active ingredient.

The cromolyn of the present invention inhibits not only the production of TGF-β and the accumulation of collagen, which is known as the major secretion marker of hepatic stellate cells, but also hepatocyte migration caused by the treatment of hepatocytes with TGF-β and decrease in E-cadherin expression caused by EMT progression. Further, it has an anti-senescence effect on hepatocytes. From the above, cromolyn has the dual effect of inhibiting the activity of HSCs and promoting the recovery of hepatocyte function, and thus can be used as health food for preventing and ameliorating various liver diseases.

There is no limitation to the type of food to which the cromolyn of the present invention is added. Examples of foods to which the cromolyn can be added are drinks, meat, sausage, bread, biscuit, rice cake, chocolate, candy, snacks, confectioneries, pizza, ramen, other noodles, gums, dairy products including ice cream, all sorts of soup, beverages, alcoholic beverages and vitamin complex, dairy products and processed dairy products, etc. and include all health foods which fall under the general definition.

The cromolyn of the present invention can be added to food as is or can be used together with other foods or food ingredients, and can be appropriately used according to the conventional methods. The mixed amount of active ingredients can be properly determined depending on the purpose of use (prevention or amelioration). Generally, the amount of the above compound added to health foods can be 0.1-90 parts by weight. However, in case of a long-term intake for the purpose of health and hygiene, or control of health, the above amount could be below the above range, and could be used in excess of the above range since there are no safety issues.

In a case where the composition for health food according to the present invention is a composition for a beverage, there is no specific limitation to the ingredient other than containing the above compound as an essential component at the designated ratio. Further, the composition may contain various flavors or natural carbohydrates, etc. as additional ingredients, like conventional beverages. Examples of the natural carbohydrates can be common saccharides such as monosaccharides (e.g., glucose, fructose, etc.); disaccharides (e.g., maltose, sucrose, etc.); and polysaccharides (e.g., dextrin, cyclodextrin, etc.), and glucose alcohol such as xylitol, sorbitol, erythritol, etc. Other than the flavors mentioned above, natural flavors (thaumatin, *stevia* extract (e.g., rebaudioside A, glycyrrhizin, etc.) and synthetic flavors (saccharin, aspartame, etc.) can be advantageously used as a flavor. The ratio of natural carbohydrates is generally about 1 to 20 g, preferably about 5 to 10 g, per 100 of the composition of the present invention.

Further, the health food composition according to the present invention can contain various nutritional supplements, vitamins, minerals (electrolytes), flavors such as synthetic flavor and natural flavor, coloring agents and appetizers (cheese, chocolate, etc.), pectic acid and its salts, alginic acid and its salt, organic acids, protective colloid, which is a viscosity agent, pH regulator, stabilizer, preservative, glycerin, alcohol, carbonation agent used in soft drinks, etc. Besides, the composition can contain flesh for the preparation of natural fruit juice and fruit juice and vegetable drink.

The above ingredients can be used individually or in a combination. The proportion of the additives is not limited, but is generally selected from 0.1 to about 20 parts by weight per 100 parts by weight of the cromolyn of the present invention.

In the following, the present invention will be described in detail with reference to the working examples, experimental examples, and preparation examples.

However, the following working examples, experimental examples, and preparation examples merely exemplify the present invention, and the present invention is not limited by the following working examples, experimental examples, and preparation examples.

<Example 1> Cell Culture and Preparation of the Compound

The experiment was performed by using the LX-2 and HCT-T6 cell lines provided by Professor Sang-Hyun Seung's research team (Seoul National University) and S. L. Friedman's research team (School of Medicine at Mount Sinai, USA), respectively, as the hepatic stellate cells (HSC) of the present invention. Specifically, the experiment was conducted by growing the cells at 37° C. and 5% $CO_2$ in DMEM (Dulbecco's Modified Eagle Medium) to which 10% of heat inactivated fetal bovine serum and 1% of penicillin and streptomycin were added.

Further, the experiment on hepatocytes was conducted by isolating the primary hepatocyte from the liver of a male C57BL6 mouse of around 6 weeks old.

Furthermore, ionomycin and cromolyn (cromoglicic acid) were purchased from Cayman Chemical Company (Ann Arbor, USA) and Santa Cruz Biotechnology (Santa Cruz, USA), respectively, and they were used after dissolving in DMSO (dimethylsulfoxide) for the in vitro experiments.

<Experimental Example 1> Selection of Anti-Liver Cirrhosis Candidate Agents Using the Connectivity Map GEO data was used to confirm the therapeutic signature of liver fibrosis or liver cirrhosis based on the gene expression profile.

Specifically, to identify the profile of gene expression relating to liver fibrosis or liver cirrhosis, among the GEO data provided by the NCBI, the microarray data of the liver samples of liver cirrhosis from 40 patients and normal liver samples from 6 people from GSE25097 were used. First of all, probe ID of which the intensity was changed 2.5 times or more was extracted. Then, the probe ID was combined to the gene symbols. In order to produce the connectivity map, upregulated genes (710 genes) or downregulated genes (225 genes) were separated from the 2,226 gene symbols to which the above probe ID was combined by applying 'log FC>|1.5|' threshold fold-change to the livers suffering from liver cirrhosis, and then listed. Further, each gene symbol of the two separated groups was converted into probe ID corresponding to analytical Affymetrix HG U133A. Meanwhile, the connectivity map was performed by using the method disclosed in Lamb J, Crawford E D, Peck D, et al. The connectivity map: using gene-expression signatures to connect small molecules, genes, and disease. Science. 2006; 313: 1929-35.

As a result, as shown in Table 1, 20 candidate agents, which can cure liver cirrhosis into a normal, healthy state, were discovered by using the connectivity map (Table 1).

Further, among the top 20 candidate agents, cromoglicic acid (cromolyn; CID 2882), MK-801 (Dizocilpine; CID 180081), iopanoic acid (CID 3735), ionomycin (CID 6912226), and tolazamide (CID 5503), which have significant p-values, were identified. Among the five candidate agents above, MK-801 is a non-competitive antagonist of the glutamate receptor, tolazamide is used by patients suffering from type II diabetes by controlling glucose, and iopanoic acid was developed to inhibit early deiodinase enzymes. However, MK-801, tolazamide, and iopanoic acid were prohibited from being used for treatment due to their side effects in USA, and have the potential to cause side effects to patients suffering from liver cirrhosis. Therefore, in the present invention, the following experiments were conducted using cromolyn and ionomycin.

TABLE 1

| rank | cmap name | enrichment | p |
|---|---|---|---|
| 1 | MG-132 | 0.997 | — |
| 2 | phenanthridinone | 0.989 | — |
| 3 | gefitinib | 0.941 | — |
| 4 | cromoglicic acid | 0.929 | 0.00964 |
| 5 | splitomicin | 0.906 | — |
| 6 | 2-deoxy-D-glucose | 0.897 | — |
| 7 | cantharidin | 0.894 | — |
| 8 | dexverapamil | 0.848 | — |
| 9 | celastrol | 0.826 | — |
| 10 | (−)-MK-801 | 0.817 | 0.00205 |
| 11 | iopanoic acid | 0.815 | 0.00223 |
| 12 | ionomycin | 0.805 | 0.015 |
| 13 | flavoxate | 0.803 | — |
| 14 | trazodone | 0.795 | — |
| 15 | tracazolate | 0.79 | — |
| 16 | tolazamide | 0.789 | 0.01921 |
| 17 | 4,5-dianilinophthalimide | 0.78 | — |
| 18 | pararosaniline | 0.779 | — |
| 19 | DL-thiorphan | 0.777 | — |
| 20 | 5252917 | 0.775 | — |

<Experimental Example 2> Identification of the Cytotoxic Effects Against Hepatic Stellate Cells <2-1> Identification of the Effect on Cell Proliferation Using a MTT Assay To confirm the proliferation activity on hepatic stellate cells, a MTT (3-(4,5-dimethylthiazol-2-yl)-2,5-diphenyltetrazolium bromide) assay was performed, and the HSC-T6 and LX2 cell lines obtained from <Example 1> above were used as hepatic stellate cells.

Specifically, the MTT assay was performed by seeding the cell suspensions of each cell onto a 96-well plate at a density of $5\times10^4$ cells/well. Then, the MIT stock solution (5 mg/mL) in which MTT was dissolved in PBS (phosphate-buffered saline, pH 7.2) was prepared, and 15 μL of the MTT solution was added to each well after filtration. After culturing for 4 hours at 37° C. and 5% $CO_2$, the reaction was terminated by adding 185 μL of solubilization solution to each well, and then the cell viability was measured at an absorbance of 620 nm using an ELISA (enzyme-linked immunosorbent assay) reader. Furthermore, cell viability was measured by calculating the ratio of absorbance of the cells treated/untreated with the candidate agents.

As shown in FIG. 2, as the levels of cromolyn and ionomycin increased, the proliferation activity was confirmed to decrease as compared to the untreated control group. While in the HSC-T6 cell line a low level (0.1 μM) of cromolyn and ionomycin treatment did not show a significant effect, in the LX2 cell line an anti-proliferation effect was confirmed even at the low level (0.1 μM) (FIGS. 2A and B).

<2-2> Confirmation of the Cytotoxic Effect Using a LDH (Lactate Dehydrogenase) Assay To confirm whether the above result from the MTT assay in section <2-1> above showed a reduced MTT value due to cell death, the cytotoxicities of cromolyn and ionomycin were confirmed through a LDH assay.

Specifically, while gradually increasing the amounts of cromolyn and ionomycin in an independent cell culture medium, the amount of LDH released into the above culture medium was measured, and the experiment was conducted by using a LDH cytotoxicity assay kit (Cayman Chemical, USA) according to the method provided by the manufacturer. First, the cells were grown in DMEM (Dulbecco's Modified Eagle Medium), to which 10% of heat inactivated fetal bovine serum and 1% of penicillin and streptomycin were added, at 37° C. and 5% $CO_2$. Then, the above cells were seeded in a 96-well plate at a density of $2\times10^4$/well. Cromolyn and ionomycin were added thereto in increasing amounts. After 48 hours, 100 μL of the supernatant from each well was transferred to the new plates, 100 μL of the reaction solution was added to each well, the plate was incubated with gentle shaking on an orbital shaker for 30 minutes at the room temperature, and then the absorbance was measured at 490 nm with a plate reader.

As a result, as shown in FIGS. 2C and 2D, cromolyn showed no cytotoxicity except at the high level (10 μM), while ionomycin was confirmed to induce cell death in a concentration dependent manner.

As such, since ionomycin has the potential of cytotoxicity, the present invention selected cromolyn as the final candidate and conducted the following experiments.

<Experimental Example 3> Confirmation of Cromolyn's Inhibitory Effect on the Production of Collagen and TGF-β

To confirm whether cromolyn inhibits the production of TGF-β and the accumulation of collagen, which are known as the major secretion marker of activated HSCs, LX-2 and HCT-T6 cell lines were analyzed by ELISA.

Specifically, collagen was detected by using the Sirius Red Total Collagen Detection Kit (Chondrex, USA). The suspended cells were seeded in a 24-well plate at a density of $1\times10^4$ cells/well, and treated with various amounts of cromolyn for 48 hours. Then, the diluted solutions or standard samples were added to 1.5-mL centrifuge tubes in duplicate. Subsequently, each tube was incubated for 20 minutes at room temperature together with 500 μl of the Sirius Red solution. The supernatant was removed, the tubes were washed twice, and 200 μL of the final supernatant was transferred to a 96-well plate. The optical density was measured at 510-550 nm.

Figure 3A:
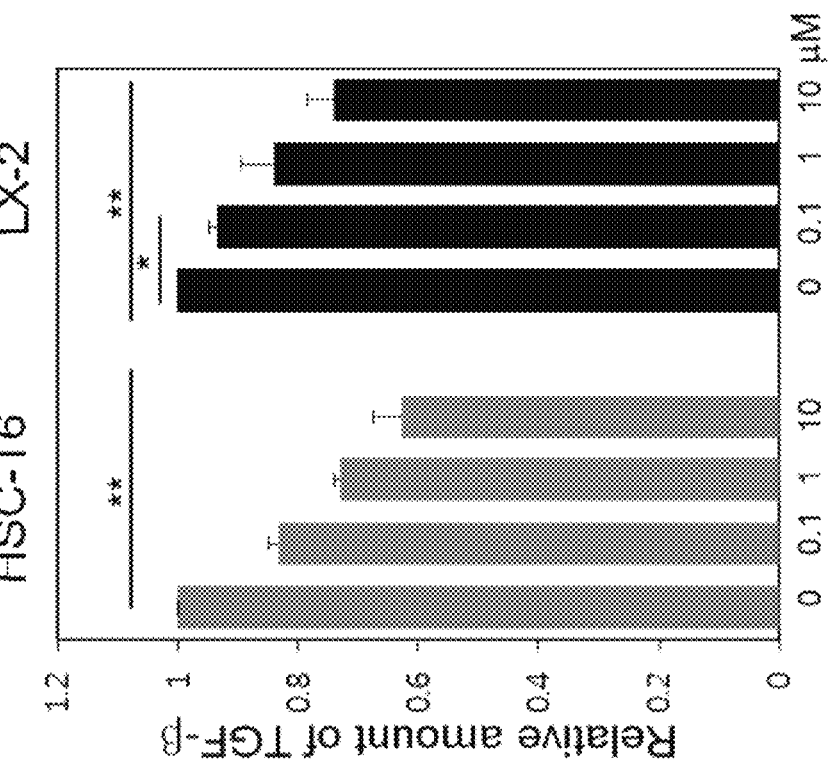
FIGS. 3A and 3B verify the changes in the levels of secreted collagen and TGF-β of hepatic stellate cell line after treatment with cromolyn.
Figure 3B:
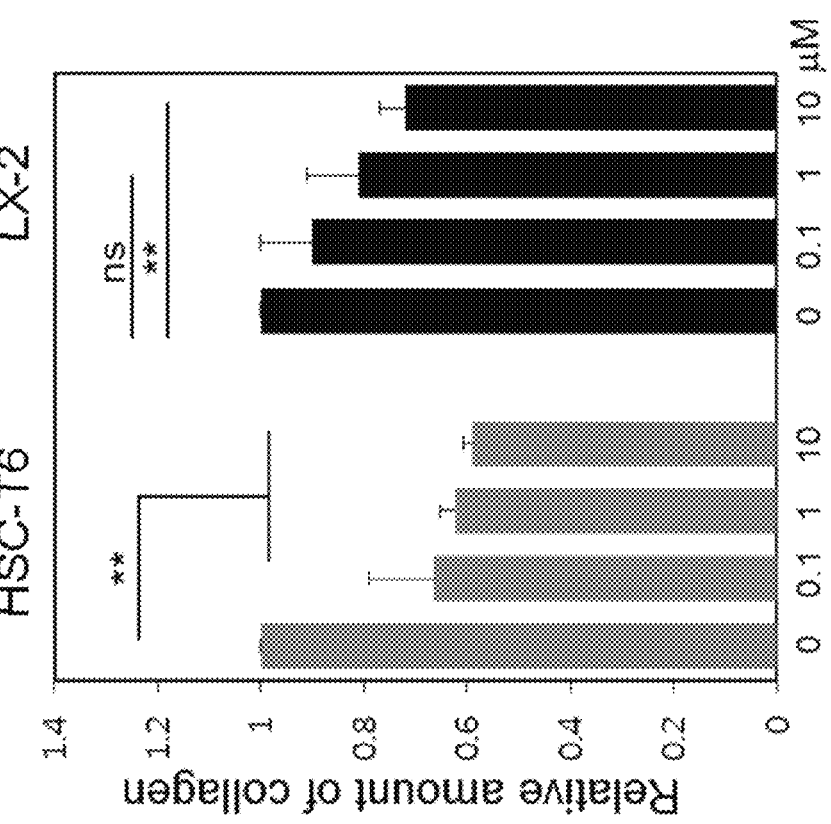

As a result, as shown in FIGS. 3A and 3B, as the level of cromolyn increases, the released collagen significantly decreases. Further, through ELISA, cromolyn was confirmed to inhibit the production of TGF-β in a concentration-dependent manner (FIGS. 3A and B).

<Experimental Example 4> Confirmation of the Inhibitory Effect of Cromolyn on EMT (Epithelial-Mesenchymal Transition) of Hepatocytes The effect of cromolyn on restoration in hepatocytes was verified. The previous various studies showed that liver fibrosis goes through the EMT process (Iwaisako K, Brenner D A, Kisseleva T. What's new in liver fibrosis. The origin of myofibroblasts in liver fibrosis. *Journal of gastroenterology and hepatology*. 2012; 27 Suppl2: 65-8; Wiemann S U, Satyanarayana A, Tsahuridu M, et al. Hepatocyte telomere shortening and senescence are general markers of human liver cirrhosis. *FASEB journal: official publication of the Federation of American Societies for Experimental Biology*. 2002; 16: 935-42). Therefore, the present inventors confirmed the motility of primary hepatocytes by treating cromolyn in the presence and absence of TGF-β, which induces EMT.

Specifically, cell motility according to treatment with cromolyn was analyzed by using the known wound assay in the presence and absence of TGF-β (2 ng/mL), and the healing distance of the wound was measured by a LDH assay. Further, after treating with TGF-β and cromolyn, changes in the E-cadherin expression was verified, which was confirmed by treating primary hepatocytes with TGF-β (Carl Bio Chem, USA) and then conducting Western Blots using the antibody against E-cadherin (H-180) (Santa Cruz, USA). In addition, tubulin was used as the loading control.

Figure 4A:
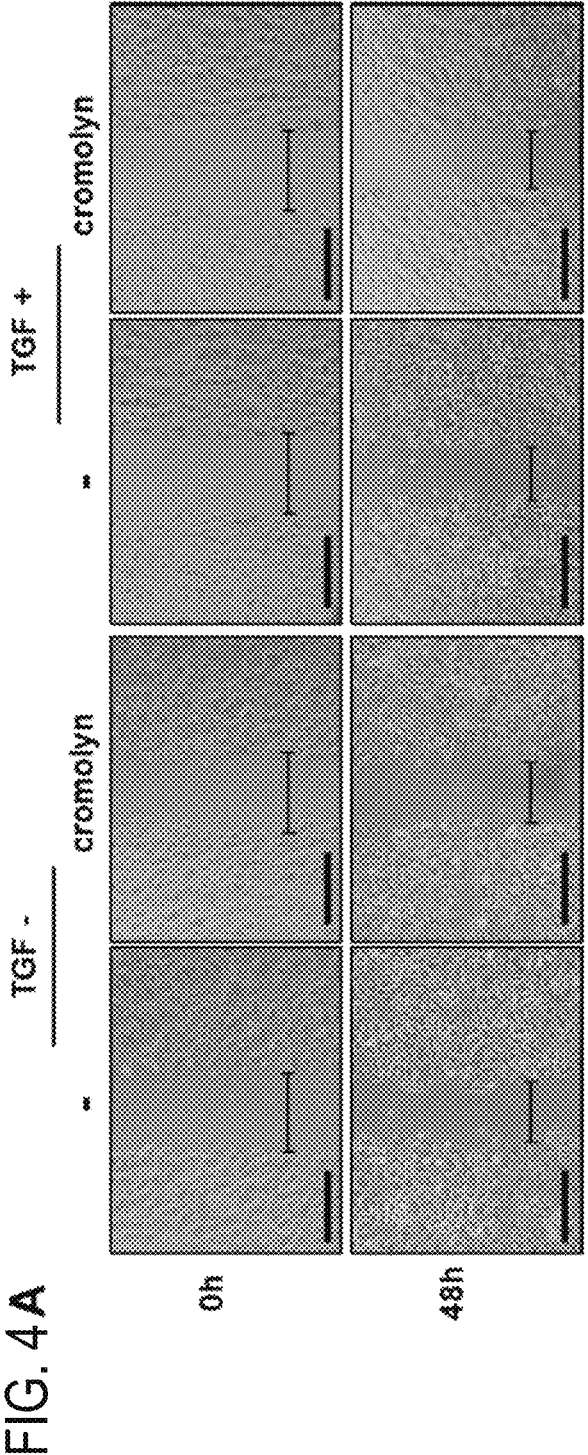
FIGS. 4A, 4B, and 4C verify the inhibitory effects on EMP (epithelial mesenchymal transition) induced by TGF-β by the treatment with cromolyn in hepatocytes.
Figure 4C:
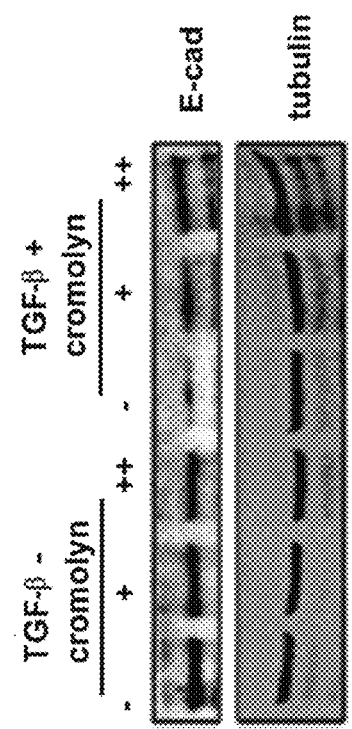
Figure 4B:
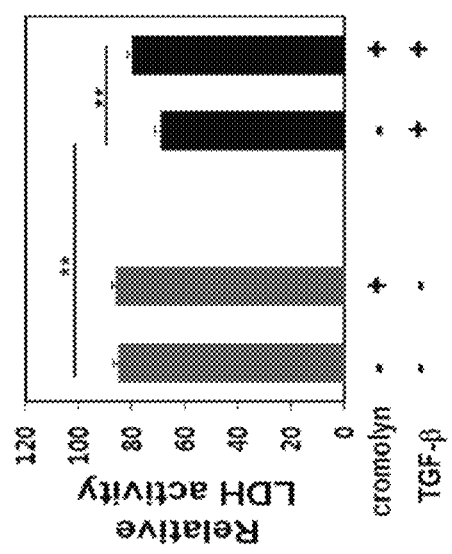

As a result, as shown in FIGS. 4A and B, in the absence of TGF-β, the motility of hepatocytes of the group treated with cromolyn did not show a significant difference as compared to the untreated control group, but in the presence of TGF-β it was confirmed that TGF-β induced the migration of hepatocytes and cromolyn effectively inhibited the migration activity of hepatocytes by 15% in terms of the migration distance. In addition, as shown in FIG. 4C, treatment with TGF-β decreased the expression level of E-cadherin (lines 1, 4 of E-cadherin), which is similar to the EMT phenomenon, but co-culture of cromolyn and hepatocytes showed to significantly inhibit the decrease in the expression of E-cadherin in a concentration-dependent manner due to the EMT progress (FIG. 4).

<Experimental Example 5> Confirmation of the Anti-Senescence Effect of Cromolyn on Hepatocytes Since senescence is a typical phenomenon of fibrosis, the anti-senescence effect of cromolyn on hepatocytes was confirmed by using β-galactosidase staining, which is a senescence index.

SA-β-gal (Senescence β-galactosidase) staining was performed by using the Senescence β-Galactosidase Staining Kit (Biovision, USA) according to the method provided by the manufacturer. Specifically, after washing with PBS, the cells were fixed by 2% formaldehyde and 0.2% glutaraldehyde in PBS for 15 minutes at room temperature. The fixed cells were washed with PBS, and incubated together with X-gal staining solution for 24 hours at 37° C. The cells were visualized, and photographs were taken with the Zeiss PALM laser capture microdissection microscope (Zeiss, Germany).

As a result, as shown in FIG. 5, three days after culturing hepatocytes in vitro, the number of β-galactosidase-positive cells increased considerably, but by the cromolyn treatment, the number of β-galactosidase-positive cells were found to decrease in a concentration-dependent manner (FIGS. 5 A and B).

Hereinafter, the preparation example for each preparation according to the present invention will be described. The below preparation examples are to help the understanding of the working of the present invention, but do not indicate that the preparation methods for the formulation according to the present invention are limited to the following preparation examples below.

<Preparation Example 1> Preparation of the Medicaments

<1-1> Preparation of Powder
cromolyn 10 mg
sucrose 100 mg
talc 10 mg

The powder was prepared by pulverizing and mixing the above ingredients, and then filling them into sealed sachets.

<1-2> Preparation of Tablets
cromolyn 10 mg
starch 100 mg
sucrose 100 mg
magnesium stearate 2 mg According to the general preparation method for tablets, tablets were prepared by mixing the above ingredients, and then tableting the mixture.

<1-3> Preparation of Capsules
cromolyn 10 mg
crystalline cellulose 3 mg
lactose 15 mg
magnesium stearate 1 mg According to the general preparation method for capsules, capsules were prepared by mixing the above ingredients, and then filling the mixture into gelatin capsules.

<1-4> Preparation of Granules
cromolyn 10 mg
soybean extract 50 mg
glucose 200 mg
starch 500 mg After mixing the above ingredients, the granules were prepared by adding 100 mL of 30% ethanol to the mixture, forming granules by drying at 60, and then filling into sachets.

<1-5> Preparation of Pills
cromolyn 10 mg
lactose 1,500 mg
glycerin 1,500 mg
starch 980 mg After mixing the above ingredients, the pills were prepared to contain 4 g per 1 pill according to the general preparation methods for pills.

<1-6> Preparation of Injections
cromolyn 10 mg
mannitol 180 mg
sterilized distilled water for injection 2,870 mg
$Na_2HPO_4 12H_2O$ 30 mg According to the general preparation method for injections, the injection was prepared by mixing the above ingredients so that one ample contains 2 mL.

<1-7> Preparation of Liquid Formulations
cromolyn 10 mg
isomerized glucose syrup 10,000 mg
mannitol 5,000 mg
purified water q.s.

According to the general preparation method for liquid formulations, the liquid formulation was prepared by dissolving the above ingredients in purified water, adding a proper scent thereto, and then filling the resulting product in a bottle and sterilizing it.

Preparation Example 2: Preparation of Food Products

<2-1> Preparation of Food Products from Wheat Flour 0.5-5.0 parts by weight of the cromolyn of the present invention was added to wheat flour and, by using the thus-obtained mixture, bread, cake, cookies, crackers, and noodles were prepared.

<2-2> Preparation of Soup and Gravies

By adding 0.1-5.0 parts by weight of the cromolyn of the present invention to soup and gravies, soup and gravies for noodles and processed meat products for health were prepared.

<2-3> Preparation of Ground Beef

Ground beef for health was prepared by adding 10 parts by weight of the cromolyn of the present invention to ground beef.

<2-4> Preparation of Dairy Products 5-10 parts by weight of the cromolyn of the present invention was added to milk, and various dairy products such as butter and ice cream were prepared by using the thus-obtained milk.

<2-5> Preparation of Sunsik (Powder Made of Mixed Grains)

What is claimed is:

1. A method for preventing or treating liver cirrhosis, liver fibrosis, liver failure, or hepatitis in a subject in need thereof, comprising administering an effective amount of cromolyn or a pharmaceutically acceptable salt thereof to the subject, wherein the cromolyn is a compound represented by Formula 1:

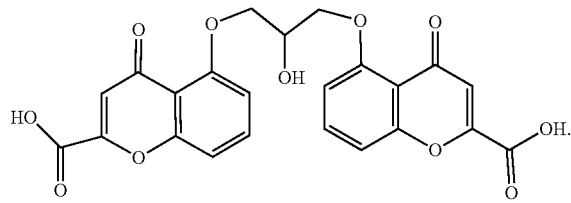

Formula 1

2. The method according to claim 1, wherein the cromolyn inhibits the accumulation of collagen in hepatic stellate cell (HSC).

3. The method according to claim 1, wherein the cromolyn inhibits the production of TGF-β in hepatic stellate cell.

4. The method according to claim 1, wherein the cromolyn inhibits the decrease in expression of E-cadherin in hepatocyte.

5. The method according to claim 1, wherein the cromolyn has anti-senescence activity on hepatocytes.

6. The method according to claim 1, wherein the cromolyn inhibits the activity of hepatic stellate cell and recovers a hepatocyte function.

* * * * *